(12) United States Patent
Shawver et al.

(10) Patent No.: US 6,649,548 B1
(45) Date of Patent: Nov. 18, 2003

(54) NONWOVEN WEB AND FILM LAMINATE WITH IMPROVED STRENGTH AND METHOD OF MAKING THE SAME

(75) Inventors: Susan Elaine Shawver, Roswell, GA (US); Hughey Kenneth Jeffries, Marietta, GA (US); Simon Kwame Ofosu, Lilburn, GA (US); Jay Sheldon Shultz, Roswell, GA (US); Peter Michlovich Kobylivker, Marietta, GA (US); Dwyana Marchael Barrett, Canton, GA (US); Patrick John Notheis, Menasha, WI (US); Stephen Carl Meyer, Green Bay, WI (US); Nathan Allen Genke, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/404,561

(22) Filed: Sep. 23, 1999

Related U.S. Application Data

(60) Provisional application No. 60/102,733, filed on Oct. 2, 1998.

(51) Int. Cl.[7] .......................... B32B 27/12; B32B 27/32
(52) U.S. Cl. .................. 442/398; 442/327; 442/381; 442/382; 442/394
(58) Field of Search ................. 442/327, 381, 442/382, 394, 398

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,538 A | 3/1970 | Petersen et al. | 161/150 |
| 3,502,763 A | 3/1970 | Hartmann et al. | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 3,855,046 A | 12/1974 | Hansen et al. | 161/150 |
| 4,041,203 A | 8/1977 | Brock et al. | 428/157 |
| 4,340,563 A | 7/1982 | Appel et al. | 264/518 |
| 4,374,888 A | 2/1983 | Bornslaeger | 428/198 |
| 4,379,102 A | 4/1983 | Kertscher | 264/40.7 |
| 4,542,199 A | 9/1985 | Kaminsky et al. | 526/160 |
| 4,652,487 A | 3/1987 | Morman | 428/138 |
| 4,655,760 A | 4/1987 | Morman et al. | 604/385 |
| 4,657,802 A | 4/1987 | Morman | 428/152 |
| 4,720,415 A | 1/1988 | Vander Wielen et al. | 428/152 |
| 4,725,473 A | 2/1988 | Van Gompel et al. | 428/156 |

(List continued on next page.)

FOREIGN PATENT DOCUMENTS

| | | | |
|---|---|---|---|
| CA | 1159601 | 7/1966 | D04H/3/05 |
| EP | 0400333 B1 | 12/1990 | 297/8 |
| EP | 0444671 A2 | 9/1991 | 297/8 |
| EP | 0472946 A2 | 3/1992 | 297/8 |
| EP | 0685586 A2 | 12/1995 | D04H/13/00 |
| WO | 96/19346 | 6/1996 | B32B/7/00 |
| WO | 98/29246 | 7/1998 | B32B/27/12 |

OTHER PUBLICATIONS

Encyclopedia of Polymer Science and Engineering, vol. 3, "Cellular Materials to Composites", A Wiley–Interscience Publication, John Wiley & Sons; 1985, pp. 299–300.

(List continued on next page.)

*Primary Examiner*—Elizabeth M. Cole
*Assistant Examiner*—Norca L. Torres
(74) *Attorney, Agent, or Firm*—Steven D. Flack

(57) ABSTRACT

There is disclosed a nonwoven web/film laminate for use as a fabric in personal care products. The laminate is formed of at least two layers in an SF formation. The spunbond (S) layer of the laminate is formed of preferably metallocene catalyzed polypropylene. The film (F) layer is formed of a polyolefin which may be metallocene-catalyzed.

9 Claims, 3 Drawing Sheets

U.S. PATENT DOCUMENTS

| | | | | |
|---|---|---|---|---|
| 4,777,073 | A | 10/1988 | Sheth | 428/155 |
| 4,781,966 | A | 11/1988 | Taylor | 428/152 |
| 4,789,699 | A | 12/1988 | Kieffer et al. | 524/271 |
| 4,810,571 | A | 3/1989 | Guthrie | 428/286 |
| 4,818,600 | A | 4/1989 | Braun et al. | 428/290 |
| 4,937,299 | A | 6/1990 | Ewen et al. | 526/119 |
| 4,965,122 | A | 10/1990 | Morman | 428/225 |
| 4,981,747 | A | 1/1991 | Morman | 428/198 |
| 5,064,802 | A | 11/1991 | Stevens et al. | 502/155 |
| 5,145,727 | A | 9/1992 | Potts et al. | 428/198 |
| 5,169,706 | A | 12/1992 | Collier, IV et al. | 428/152 |
| 5,178,931 | A | 1/1993 | Perkins et al. | 428/198 |
| 5,188,885 | A | 2/1993 | Timmons et al. | 428/198 |
| 5,189,192 | A | 2/1993 | LaPointe et al. | 556/11 |
| 5,226,992 | A | 7/1993 | Morman | 156/62.4 |
| 5,266,392 | A | 11/1993 | Land et al. | 428/224 |
| 5,281,679 | A | 1/1994 | Jejelowo et al. | 526/114 |
| 5,302,454 | A | 4/1994 | Cecchin et al. | 428/402 |
| 5,336,545 | A | 8/1994 | Morman | 428/152 |
| 5,349,100 | A | 9/1994 | Mintz | 585/350 |
| 5,352,749 | A | 10/1994 | DeChellis et al. | 526/68 |
| 5,368,927 | A | 11/1994 | Lesca et al. | 428/288 |
| 5,374,696 | A | 12/1994 | Rosen et al. | 526/126 |
| 5,382,630 | A | 1/1995 | Stehling et al. | 525/240 |
| 5,393,599 | A | 2/1995 | Quantrille et al. | 428/284 |
| 5,416,228 | A | 5/1995 | Ewen et al. | 556/7 |
| 5,464,688 | A | 11/1995 | Timmons et al. | 428/298 |
| 5,468,440 | A | 11/1995 | McAlpin et al. | 264/291 |
| 5,529,850 | A | 6/1996 | Morini et al. | 428/500 |
| 5,549,867 | A | 8/1996 | Gessner et al. | 264/555 |
| 5,571,619 | A | 11/1996 | McAlpin et al. | 428/364 |
| 5,612,123 | A | 3/1997 | Gessner et al. | 442/401 |
| 5,624,425 | A | 4/1997 | Gray et al. | 604/385.2 |
| 5,624,621 | A | 4/1997 | Asanuma et al. | 264/176.1 |
| 5,672,415 | A | 9/1997 | Sawyer et al. | 428/219 |
| 5,695,849 | A | 12/1997 | Shawver et al. | 428/131 |
| 5,707,468 | A | 1/1998 | Arnold et al. | 156/62.6 |
| 5,709,921 | A | 1/1998 | Shawver | 428/152 |
| 5,723,217 | A | 3/1998 | Stahl et al. | 428/401 |
| 5,723,546 | A | 3/1998 | Sustic et al. | 525/240 |
| 5,726,103 | A | 3/1998 | Stahl et al. | 442/59 |
| 5,736,219 | A | 4/1998 | Suehr et al. | 428/113 |
| 5,736,465 | A | 4/1998 | Stahl et al. | 428/298 |
| 5,763,080 | A | 6/1998 | Stahl et al. | 428/378 |
| 5,763,532 | A | 6/1998 | Harrington et al. | 525/194 |
| 5,910,136 | A | 6/1999 | Hetzler et al. | 604/367 |
| 6,037,281 | A | * | 3/2000 | Mathis et al. | 442/394 |
| 6,060,009 | A | * | 5/2000 | Welygan et al. | 264/167 |
| 6,177,607 | B1 | * | 1/2001 | Blaney et al. | 442/370 |
| 6,187,696 | B1 | * | 2/2001 | Lim et al. | 442/77 |
| 6,420,625 | B1 | * | 7/2002 | Jones et al. | 604/267 |

OTHER PUBLICATIONS

Encyclopedia of Polymer Science and Engineering, vol. 8, "Identification to Lignin", A Wiley–Interscience Publication, John Wiley & Sons; 1987, pp. 162–179.

Exxon Chemical Company, EXXPOL™ Technology, Nonwovens, "Achieve ™ Propylene Polymers for Spunbond Nonwovens—Fact Sheet", 2 pages.

Exxon Chemical Company, EXXPOL™ Technology, Nonwovens, "Achieve™ Propylene Polymers vs. Conventional PP—Fact Sheet", 2 pages.

Exxon Chemical Company, Products from EXXPOL™ Technology, "Achieve 3835—Propylene Polymer for Nonwovens Fiber and General Extrusion", Oct. 1995.

Kenneth Mason Publications, "Advantages of Metallocene ethylene polymer resins in multilayer blown and cast stretch films", *Research Disclosure*, 1998, Issue 412, pp. 1077–1087.

McAlpin, J.J. et al., "Applications Potential of EXXPOL™ Metallocene—Based Polypropylene" © Copyright Exxon Corp 1994, pp. 1–8 with Figures 1–11 and Tables 1–5.

"Metallocenes Market Sizzles with New Products, Ventures", *Chemical Engineering*, Oct. 1995, pp. 51–52.

Reuter Business Alert, "USA: Exxon Chemical—First Commercial Scale Production Run of Metallocene–Based PP Successfully Completed " *Chemical Marketing Reporter*, Sep. 18, 1995, Copyright 1995 Schnell Publishing Co., 3 pages.

Richeson, G.C. et al., "Advances in Metallocene Propylene Polymers for Spunbond", *Nonwovens World*, 1998, vol. 7, No. 4, pp. 76–83.

Scott, N.D., "Metallocenes and polypropylene—new solutions to old problems in textile end–uses?", *Chemical Fibers International*, –/M–MF Yearbook (8–9), vol. 47, Apr. 1997, pp. 123–124.

Stahl, G.A. et al., "Applications Potential in Nonwovens of EXXPOL™ Metallocene—Based Propylene Polymers", Presentation at TANDEC Conference, © Copyright Exxon Corp 1994, 13 pages.

* cited by examiner

NONWOVEN WEB AND FILM LAMINATE WITH IMPROVED STRENGTH AND METHOD OF MAKING THE SAME

This application claims priority from U.S. Provisional Application No. 60/102,733 filed on Oct. 2, 1998.

FIELD OF THE INVENTION

The present invention relates to nonwoven web and film laminates with improved strength. More particularly, the present invention relates to laminates for use in disposable garments and personal care products with improved tear resistance, and to a method of manufacturing such laminates.

BACKGROUND OF THE INVENTION

Industry has long recognized the benefits of combining barrier properties of films and cloth-like attributes of nonwoven fabrics for various medical, personal care and commercial applications. Furthermore, such web/film laminates may also exhibit certain levels of elasticity, and when incorporating stretched filled microporous film, breathability. Therefore, laminates have been produced using both film and nonwoven web materials.

Lamination of films has been used to create materials which are both impervious and somewhat cloth-like in appearance and texture. Uses for such laminates include the outer covers for personal care products such as diapers, training pants, incontinence garments, and feminine hygiene products. In this regard, reference may be had to coassigned U.S. Pat. No. 4,818,600 dated Apr. 4, 1989 and U.S. Pat. No. 4,725,473 dated Feb. 16, 1988. Additionally, such materials are particularly suited for use in protective outer wear such as coveralls, and surgical garments and drapes. See in this regard coassigned U.S. Pat. No. 4,379,102 dated Apr. 5, 1983.

A primary purpose of the film in such laminations is to provide barrier properties. There is also a need for such laminates to be breathable so that they have the ability to transmit moisture vapor. Apparel made from laminates of these breathable or microporous films are more comfortable to wear by reducing the moisture vapor concentration and the consequent skin hydration underneath the apparel item.

Despite exhibiting many positive attributes, when used inappropriately or when exposed to particularly stressful conditions, laminates sometimes tear. In an attempt to create a nonwoven laminate with improved barrier properties, improved strength and with elastic attributes, but at lower costs, laminates have been developed in which the web fiber size has been reduced and polymer molecular weight distribution has been narrowed (since it affects polymer mechanical properties). For instance, it has been suggested that propylene polymers having high melt flow rate and narrow molecular weight distribution can be used to produce fibers for nonwoven webs and fabrics having superior barrier properties, tensile strength and softness. For example, U.S. Pat. No. 5,529,850 to Morini et. al. describes the preparation of crystalline polypropylene polymers having narrow molecular weight distribution, through the use of specific di- or polyesters as internal or external electron donors in polymerization reactions accompanying a catalyst component, such as an active magnesium halide and a titanium compound and al-alkyl compounds.

U.S. Pat. Nos. 5,726,103 and 5,763,080 to Stahl et al. describe fibers and fabrics incorporating lower melting propylene polymers in order to achieve a relatively strong and relatively fluid impervious fabric. In particular the Stahl patents describe propylene homopolymers and copolymers formed by metallocene catalyst systems. Such propylene polymers exhibit generally lower melting behavior than non-metallocene catalyzed propylene polymers. Stahl indicates that this low melting behavior is of use in the fabrication of fibers and fabric that depend on lower melting behavior or upon melting point differential between two fabrics to achieve bonding. Such fibers would include chenille or tufted, core and sheath. Stahl indicates that fabrics such as spunbond and meltblown nonwovens, when combined in spunbond/meltblown/spunbond (SMS) fabrics will show bonding at lower temperatures, and in particular, allow for the making of a higher melting fiber into a meltblown and a lower melting fiber into a spunbond. In the prospective examples of the Stahl patents, Stahl indicates that the overall strength of the fabric samples utilizing metallocene-catalyzed polypropylene in the spunbond layers will be as high as controls (which are unbonded SM fabrics). In a further prospective example utilizing one metallocene-catalyzed homopolymer polypropylene "S" layer and a commercial 1100 mfr polypropylene "M" layer, the prospective fabric would have improved barrier and filtration properties with no loss of laminated fabric strength when compared to the control. Each of these patents do not provide for better than expected tear strength in a film/nonwoven laminate.

U.S. Pat. No. 5,723,217 to Stahl et al. describes polyolefin fibers and their fabrics. This Stahl patent discusses fibers made from reactor grade isotactic poly-alpha-olefin wherein polypropylene is produced by single site catalysis. Stahl asserts that the polypropylene fibers produced will generally be stronger or have higher tenacity than conventional polymer when drawn to a fine diameter. Stahl also asserts that meltblown and or spunbond fabric containing the fiber will gain extra strength but does not allude to any method for creating a breathable film laminate with enhanced tear strength.

U.S. Pat. No. 5,612,123 to Gessner et al. describes a distribution enhanced polyolefin product. In particular this patent discusses that improved meltspinning productivity is achieved by employing polyolefin resins having key molecular weight distributions and Theological property parameters within predetermined ranges. Such polyolefin filaments and the single layer spunbond fabric prepared by the process exhibited high tenacity and tear property values. This patent also fails to allude to a method for increasing the tear properties of a breathable film laminate.

U.S. Pat. No. 5,464,688 to Timmons et al. describes nonwoven web laminates with improved barrier properties. Such webs are formed with commercially acceptable polymer with reduced molecular weight distribution in the meltblown layer of an SMS.

While metallocene-catalyzed polypropylene has heretofore been used in laminates, specifically as part of stretch bonded laminates and necked bonded laminates, the structural components, physical attributes and bonding processes of these laminates are markedly different from breathable film laminates. Furthermore, tear measurement tests, such as grab tensile/peak energy for necked bonded (NBL) and stretch bonded laminates (SBL), as well as a single spunbond layer show a higher peak energy value (in the machine direction) for Ziegler-Natta catalyzed polypropylene spunbond than for metallocene-catalyzed spunbond in these laminates. One would therefore not expect that spunbond with narrow molecular weight distribution would significantly increase tear strength in a breathable film/nonwoven web laminate.

Therefore, despite the improvements in the nonwoven laminate area, there exists a need for a breathable film/nonwoven web laminate which demonstrates increased tear strength without the addition of significant cost. Further, there exists a need for a method for producing such a laminate composite which can be done in-line at high speeds and over a short time span. Finally, there is a need for personal care products and other garments which utilize such laminates in their composite constructions. It is to the provision of such composite and method that the present invention is directed.

SUMMARY

An object of the present invention is to provide a nonwoven web/film laminate material which exhibits significant tear strength attributes.

A still further object is to provide a nonwoven web/film laminate embodying the above-discussed features which utilizes relatively inexpensive materials to increase strength properties.

A still further object is to provide an in-line process for preparing a nonwoven web/film laminate which allows for increased tear strength in the finished laminate.

A specific object resides in providing a material having many of the previously identified attributes which can be advantageously used in personal care products.

The present invention relates to a film/nonwoven web laminate including at least one nonwoven web layer having a narrow molecular weight distribution and a film.

In one embodiment of the present invention, the film is a stretched microporous film that includes an elastomeric resin and a film filler.

The present invention is also directed to a process for producing a laminate including at least one nonwoven web layer having a narrow molecular weight distribution and a film including the steps of forming a nonwoven web of a metallocene-catalyzed polypropylene and bonding a film layer to the newly formed nonwoven web layer within 1–30 seconds of the formation of the nonwoven web layer.

DETAILED DESCRIPTION OF THE INVENTION

Definitions

Figure 1:
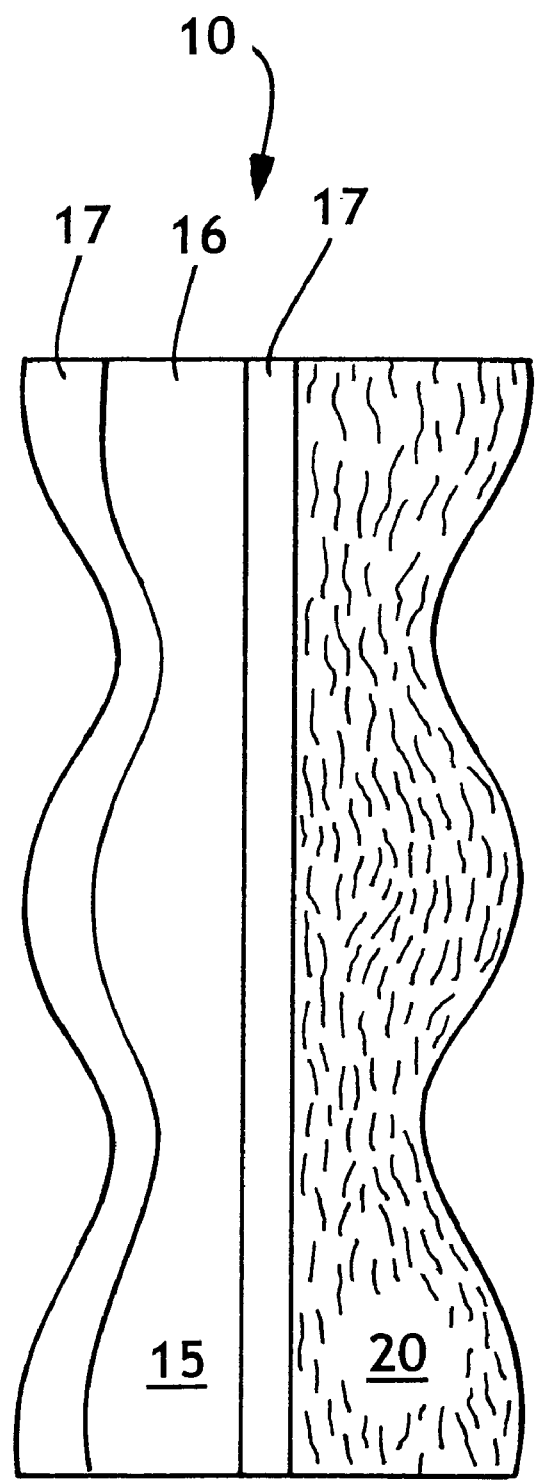
FIG. 1 is a cross-sectional view of a material embodying the features of the present invention.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein the term "spunbond fibers" refers to small diameter fibers which are formed by extruding molten thermoplastic material as filaments from a plurality of fine, usually circular capillaries of a spinneret with the diameter of the extruded filaments then being rapidly reduced as, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein the term "multilayer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Such fabrics usually have a basis weight of from about 0.1 to 12 osy (3.4 to 400 gsm), or more particularly from about 0.75 to about 3 osy. Multilayer laminates may also have various numbers of meltblown layers or multiple spunbond layers in many different configurations and may include other materials like films (F) or coform materials, e.g. SMMS, SM, SFS, etc.

As used herein, the term "personal care product" means diapers, training pants, absorbent underpants, adult incontinence products, and feminine hygiene products.

As used herein the term "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As is well known in the art, the spot bonding holds the laminate layers together as;well as imparts integrity to each individual layer by bonding filaments and/or fibers within each layer.

As used herein, the term "ultrasonic bonding" means a process performed, for example, by passing the fabric between a sonic horn and anvil roll as illustrated in U.S. Pat. No. 4,374,888 to Bornslaeger.

As used herein the term "composite elastic material" refers to an elastic material which may be a multicomponent material or a multilayer material in which one layer is elastic. These materials may be, for example, "stretch bonded" laminates (SBL) and "neck bonded" laminates (NBL). Conventionally, "stretch bonded" refers to an elastic member being bonded to another member while the elastic member is extended at least about 25 percent more than of its relaxed length. "Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered. Such a multilayer composite elastic material may be stretched to the extent that the nonelastic material gathered between the bond locations allows the elastic material to elongate. One type of stretch bonded laminate is disclosed, for example, by U.S. Pat. No. 4,720,415 to Vander Wielen et al., in which multiple layers of the same polymer produced from multiple banks of extruders are used. Other composite elastic materials are disclosed in U.S. Pat. No. 4,789,699 to Kieffer et al., U.S. Pat. No. 4,781,966 to Taylor and U.S. Pat. Nos. 4,657,802 and 4,652,487 to Morman and U.S. Pat. No. 4,655,760 to Morman et al.

Conventionally, "neck bonded" refers to an elastic member being bonded to a non-elastic member while the non-elastic member is extended under conditions reducing its width or necked. "Neck bonded laminate" refers to a composite material having at least two layers in which one layer is a necked, non-elastic layer and the other layer is an elastic layer. The layers are joined together when the non-elastic layer is in an extended condition. Examples of neck-bonded laminates are such as those described in U.S. Pat. Nos 5,226,992, 4,981,747, 4,965,122 and 5,336,545 to Morman.

As used herein, the term "compaction roll" means a set of rollers above and below the web to compact the web as a way of treating a just produced microfiber, particularly a spunbond web, in order to give it sufficient integrity for further processing, but not the relatively strong bonding of secondary bonding processes like through-air bonding, thermal bonding and ultrasonic bonding. Compaction rolls slightly squeeze the web in order to increase its self-adherence and thereby its integrity. As an alternative to the use of a compaction roll, a pressured targeted air stream (hot air knife) may be used to compact a recently formed web. As used herein, the term "hot air knife" or HAK means a process of pre-or primarily bonding a just produced microfiber, particularly spunbond, web in order to give it sufficient integrity, i.e. increase the stiffness of the web, for further processing, but does not mean the relatively strong bonding of secondary bonding processes like through air bonding, thermal bonding and ultrasonic bonding. A hot air knife is a device which focuses a stream of heated air at a very high flow rate, generally from about 1000 to about 10000 feet per minute (fpm) (305 to 3050 meters per minute), or more particularly from about 3000 to 5000 feet per minute (915 to 1525 m/min.) directed at the nonwoven web immediately after its formation. The air temperature is usually in the range of the melting point of at least one of the polymers used in the web, generally between about 200 and 550° F. (93 and 290° C.) for the thermoplastic polymers commonly used in spunbonding. The control of air temperature, velocity, pressure, volume and other factors helps avoid damage to the web while increasing its integrity. The HAK's focused stream of air is arranged and directed by at least one slot of about ⅛ to 1 inches (3 to 25 mm) in width, particularly about ⅜ inch (9.4 mm), serving a the exit for the heated air towards the web, with the slot running in a substantially cross-machine direction over substantially the entire width of the web. In other embodiments, there may be a plurality of slots arranged next to each other or separated by a slight gap. The at least one slot is usually, though not essentially, continuous, and may be comprised of, for example, closely spaced holes. The HAK has a plenum to distribute and contain the heated air prior to its exiting the slot. The plenum pressure of the HAK is usually between about 1.0 and 12.0 inches of water (2 to 22 mmHg), and the HAK is positioned between about 0.25 and 10 inches and more preferably 0.75 to 3.0 inches (19 to 76 mm) above the forming wire. In a particular embodiment, the HAK plenum's cross sectional area for cross-directional flow (i.e. the plenum cross sectional area in the machine direction) is at least twice the total slot exit area. Since the foraminous wire onto which spunbond polymer is formed generally moves at a high rate of speed, the time of exposure of any particular part of the web to the air discharged from the hot air knife is less than a tenth of a second and generally about a hundredth of a second in contrast with the through air bonding process which has a much larger dwell time. The HAK process has a great range of variability and controllability of many factors such as air temperature, velocity, pressure, volume, slot or hole arrangement and size, and the distance from the HAK plenum to the web. The HAK is further described in U.S. Pat. No. 5,707,468 and commonly assigned.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein, the term "machine direction" or MD means the direction of a fabric in the direction in which it is produced. The term "cross machine direction" or CD means the opposite direction of the fabric, i.e. a direction generally perpendicular to the MD.

For the purpose of this application the term "conventional" shall refer to Ziegler-Natta catalyzed propylene homopolymers and copolymers. For a further discussion of Ziegler-Natta catalyst reactions, one should refer to *the EncycloDedia of Polymer Science and Engineering*, Volume 8, page 162, published by John Wiley & Sons, Inc., 1987.

Referring to FIG. 1, the nonwoven web/film laminate 10 of the present invention may be made from polymers which are capable of being formed into film 15 and then bonded to a nonwoven web 20. The film may be newly formed or pre-formed film. The nonwoven web is preferably newly formed.

Such film forming polymers include but are not limited to extrudable thermoplastic polymers such as a polyolefin or a blend of polyolefins. More particularly, useful polyolefins include polypropylene and polyethylene. Other useful polymers include those described in U.S. Pat. No. 4,777,073 to Sheth, assigned to Exxon Chemical Patents. Inc., such as a copolymer of polypropylene and low density polyethylene or linear low density polyethylene. Additional polymers useful in the present invention include flexible polyolefins. As used herein the term "flexible polyolefin" refers to polyolefin materials containing propylene based polymer with controlled regions of atactic polypropylene units to achieve a desired crystallinity such as described in co-assigned U.S. Pat. No. 5,910,136 entitled "Oriented Polymeric Microporous Films with Flexible Polyolefins and Methods of making the Same" to Hetzler and Jacobs; the entire contents of which are incorporated herein by reference in its entirety. Further description of such flexible polyolefins can be found in U.S. Pat. No. 5,723,546 to Sustic and assigned to the Rexene Corporation.

Other useful polymers for the formation of film of the present invention include elastomeric thermoplastic polymers. Such polymers include those made from block copolymers such as polyurethanes, copolyether esters, polyamide, polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like. Specifically, the elastomeric thermoplastic polymers include: polyester elastomeric materials such as, for example, those available under the trade designation HYTREL® from E. I. du Pont de Nemours and Company; polyester block amide copolymers such as, for example, those available in various grades under the trade designation PEBAX® from ELF Atochem Inc. of Glen Rock, N.J.; and polyurethane elastomeric materials such as, for example, those available under the trademark ESTANE® from B. F. Goodrich & Co. or MORTHANE® from Morton Thiokol Corporation.

Elastomeric polymers have been used in the past for many applications but are somewhat limited by their intrinsic properties. These materials have recently been joined by a new class of polymers which demonstrate high barrier, breathability and elasticity attributes when incorporated into film. The new class of polymers is referred to as single site catalyzed polymers such as "metallocene" polymers produced according to a metallocene process.

Such metallocene polymers are available from Exxon Chemical Company of Baytown, Texas under the trade name EXXPOL® for polypropylene based polymers and EXACT® for polyethylene based polymers. Dow Chemical Company of Midland, Michigan has polymers commercially available under the name ENGAGE®. More specifically, the metallocene film forming polymers may be selected from copolymers of ethylene and 1-butene, copolymers of ethylene and 1-hexene, copolymers of ethylene and 1-octene and combinations thereof.

The laminate film layer 15 may be a multi-layered film which may include a core layer 16, or "B" layer, and one or more skin layers 17, or "A" layers on either side of the core layer. Any of the polymers discussed above are suitable for use as a core layer of a multi-layered film.

The skin layer will typically include extrudable thermoplastic polymers and/or additives which provide specialized properties to the film 15. Thus, the skin layer may be made from polymers which provide such properties as antimicrobial activity, water vapor transmission, adhesion and/or antiblocking properties. The polymers are thus chosen for the particular attributes desired. Examples of possible polymers that may be used alone or in combination include homopolymers, copolymers and blends of polyolefins as well as ethylene vinyl acetate (EVA), ethylene ethyl acrylate (EEA), ethylene acrylic acid (EAA), ethylene methyl acrylate (EMA), ethylene butyl acrylate (EBA), polyester (PET), nylon (PA), ethylene vinyl alcohol (EVOH), polystyrene (PS), polyurethane (PU), and olefinic thermoplastic elastomers which are multistep reactor products wherein an amorphous ethylene propylene random copolymer is molecularly dispersed in a predominately semicrystalline high polypropylene monomer/low ethylene monomer continuous matrix.

Suitable polymers for the "A" layer are available commercially under the trade designation "Catalloy" from the Himont Chemical Company of Wilmington, Del., and polypropylene. Specific commercial examples are Catalloy, KS 357P, KS-084P and KS-057P. Other suitable polymers include polymers which are semi-crystalline/amorphous or heterophasic in character. Such polymers are disclosed in European Patent Application EP 0444671 A3 (based on Application number 91103014.6), European Patent Application EP 0472946 A2 (based on Application number 91112955.9), European Patent Application EP 0400333 A2 (based on Application number 90108051.5), U.S. Pat. No. 5,302,454 and U.S. Pat. No. 5,368,927. For a more detailed description of films having core and skin layers see PCT WO 96/19346 to McCormack et al. assigned to common assignee which is incorporated herein by reference in its entirety.

The films can be made from breathable or non-breathable materials. Some films are made breathable by adding micropore developing filler particles to the film during the film forming process.

As used herein, a "micropore developing filler" is meant to include particulates and other forms of materials which can be added to a polymer and which will not chemically interfere with or adversely affect the extruded film made from the polymer but are able to be uniformly dispersed throughout the film. Generally, the micropore developing fillers will be in particulate form and usually will have somewhat of a spherical shape with average particle sizes in the range of about 0.5 to about 8 microns. The film will usually contain at least about 30 percent of micropore developing filler based upon the total weight of the film layer. Both organic and inorganic micropore developing fillers are contemplated to be within the scope of the present invention provided that they do not interfere with the film formation process, the breathability of the resultant film or its ability to bond to a fibrous polyolefin nonwoven web.

Examples of micropore developing fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivative, polymer particles, chitin and chitin derivatives. The micropore developing filler particles may optionally be coated with a fatty acid, such as stearic acid, or a larger chain fatty acid such as behenic acid, which may facilitate the free flow of the particles (in bulk) and their ease of dispersion into the polymer matrix. Silica-containing fillers may also be present in an effective amount to provide antiblocking properties.

Once the particle-filled film has been formed, it is then either stretched or crushed to create pathways through the film. Generally, to qualify as being "breathable" for the present invention, the resultant laminate should have a water vapor transmission rate (WVTR) of at least about 250 g/m²/24 hours as may be measured by a test method as described below. Furthermore, the films may be apertured. In forming the films, the films may be coextruded to increase bonding and alleviate die lip build-up.

Processes for forming film are generally known. The film 15 can be made from either cast or blown film equipment, can be coextruded and can be embossed if so desired. Additionally, the film 15 can be stretched or oriented by passing the film through a film stretching unit. The stretching reduces the film gauge or thickness from an initial gauge of 1.5–2.0 mils to an effective final gauge of 0.5 mils or less. Generally, this stretching may take place in the CD or MD or both.

The nonwoven web 20 as illustrated in FIG. 1, in the laminate 10 containing the film of the present invention, may be formed from a number of processes including, but not limited to, spunbonding and meltblowing processes. Such nonwoven webs can for example be necked polypropylene spunbond, crimped polypropylene spunbond, elastomeric spunbond or meltblown fabrics produced from elastomeric resins. As used herein, the term "necked" refers to constricting in at least one dimension by processes such as, for example, drawing or gathering.

Especially suitable fibers for forming the nonwoven web 20 include polymeric webs of narrow molecular weight distribution such as metallocene catalyzed polypropylene spunbond, and in particular inelastic metallocene-catalyzed polypropylene spunbond sold under the designation 3854 as available from the Exxon Chemical Company of Baytown Tex. Single site/metallocene catalyzed polypropylene are sold by Exxon under the trade name Achieve. In the practice of this invention, a single nonwoven web layer may be laminated to a film layer. An example of such is a spunbond (S)/film (F) laminate. Alternatively, a plurality of nonwoven web layers may also be incorporated into the laminate according to the present invention. Examples of such materials can include, for example, SFS multilayered laminate composites.

Figure 2:
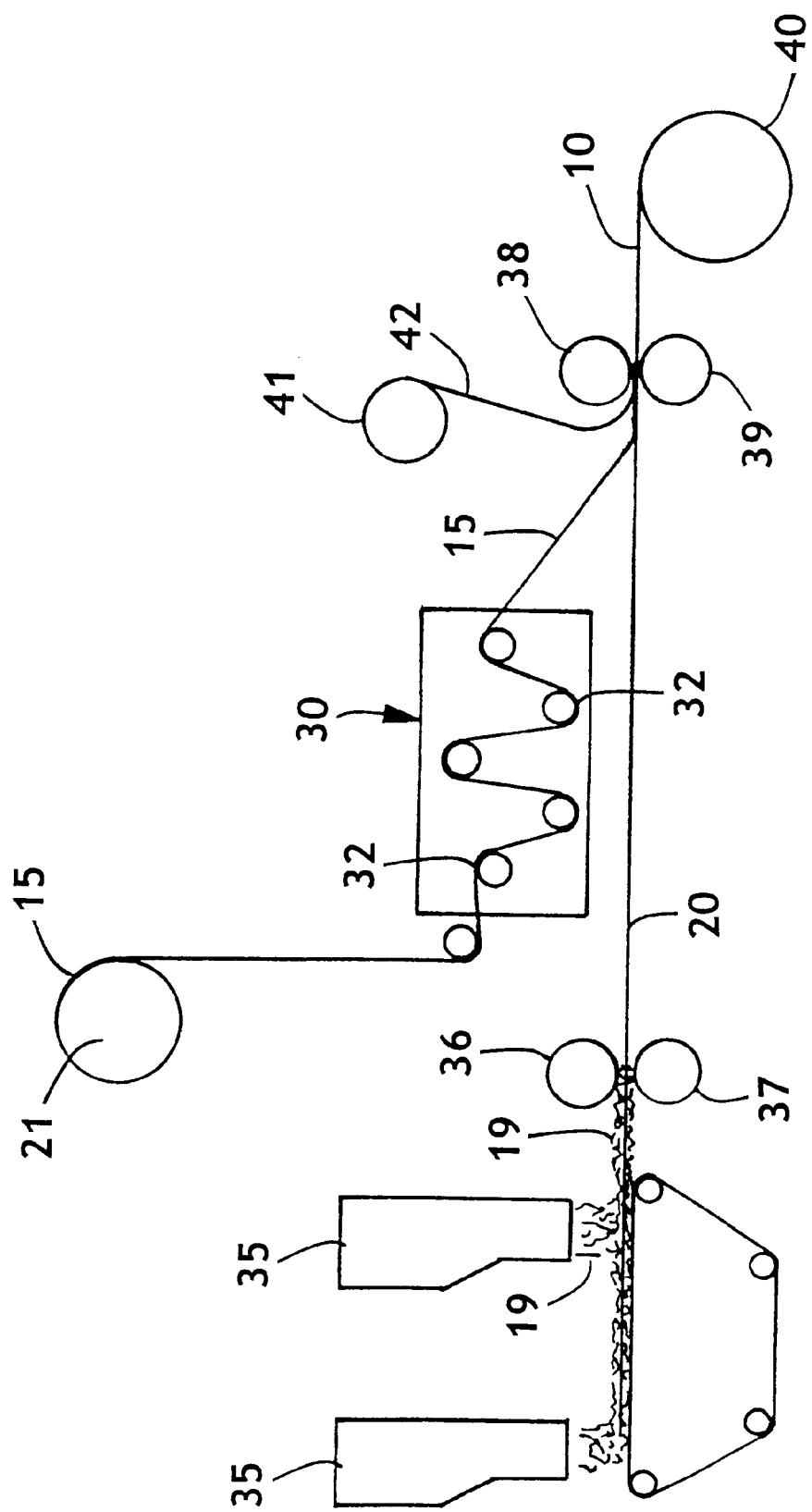
FIG. 2 is a schematic side elevation view illustrating one manner in which the material of the present invention can be prepared.

In the process of the present invention, as illustrated in FIG. 2, filled film 15 is directed from supply roll 21 to a film stretching unit 30 such as a machine direction orienter (MDO), which is a commercially available device from vendors such as the Marshall and Williams Company of Providence, Rhode Island. Such an apparatus has a plurality of stretching rollers 32 moving at progressively faster speeds relative to the pair disposed before it. These rolls apply an amount of stress and thereby progressively stretch filled film to a stretch length in the machine direction of the film which the direction of travel of filled film through the process as shown in FIG. 2. The stretch rollers may be heated for better processing. In addition, the unit may also include rolls (not shown) upstream and/or downstream from the stretch rolls that can be used to preheat the film before stretching and/anneal (or cool) it after stretching.

At the stretched length, a plurality of micropores form in the film. The film is then directed out of the apparatus so that the stress is removed in order to allow the stretched film to relax. A permanent elongation is retained after the stretched film is allowed to relax.

Alternatively, instead of being pre-formed and supplied by a supply roll, the film may itself be formed in-line. Such process is described in U.S. Provisional Patent Application entitled Process for Making a Laminate of Unaged Film and an Unaged Nonwoven Web and Products Produced Therefrom filed on Sep. 22, 1998, bearing Express Mail No. EL 54777056US and assigned to the same assignee, the entire contents of said application being incorporated herein by reference in its entirety.

A fibrous nonwoven web layer is contemporaneously formed on a conventional fibrous nonwoven web forming apparatus. As illustrated in FIG. 2, a pair of spunbond machines 35 is used to form the nonwoven web layer. Alternatively a single bank of spunbond machines may be used. The long, essentially continuous fibers are deposited onto a forming wire as an unbonded web 19 and the unbonded web is then sent through a pair of bonding rolls 36, 37 to bond the fibers together and increase the tear strength of the resultant web support layer 20. One or both of the rolls are often heated to aid in bonding. Typically, one of the rolls is also patterned so as to impart a discrete bond pattern with a prescribed bond surface area to the web. An example of a bond pattern which may be used would be the wire weave pattern. The other roll is usually a smooth anvil roll but this roll may also be patterned if desired. During the process before bonding, the spunbond web may:be compressed using a set of compaction rolls (not shown) or a hot air knife (not shown).

Once the filled film has been sufficiently stretched and the nonwoven web layer has been formed, the two layers are brought together and laminated to one another using a pair of laminating rolls 38, 39 (thermal point bonding) or other bonding means to form a breathable stretch thinned film laminate (BSTL). As with the bonding rolls, the laminating rolls may be heated. Also, at least one of the rolls may be patterned to create a discrete bond pattern with a prescribed bond surface area for the resultant laminate. Generally, the maximum bond point surface area for a given area of surface on one side of the laminate will not exceed about 50% of the total surface area. There are a number of discrete bond patterns which may be used, an example of which is the C-star or Baby Objects pattern, generally having a bond point surface area between 15 and 30%. The time between formation of the spunbond web and lamination of the web to the film is between approximately 1 and 30 seconds. See for example, Brock et al., U.S. Pat. No. 4,041,203, which is incorporated by reference in its entirety. Once the laminate exits the laminating rolls, it may be wound up into a roll for subsequent processing. Alternatively, the laminate may continue in-line for further processing or conversion.

The process shown in FIG. 2 also may be used to create a three layer web/film laminate. The only modification to the previously described process is to feed a supply of a second fibrous nonwoven web layer into the laminating rolls on a side of the filled film opposite that of the other fibrous nonwoven web layer. One or both of the nonwoven web layers may be formed directly in line as is nonwoven web layer 20. In either event, the second roll is fed into the laminating rolls as it is laminated to filled film in the same fashion as the first nonwoven web layer. Such three layer laminates are particularly useful in medical and industrial protective garment/outer workwear applications.

Figure 3:
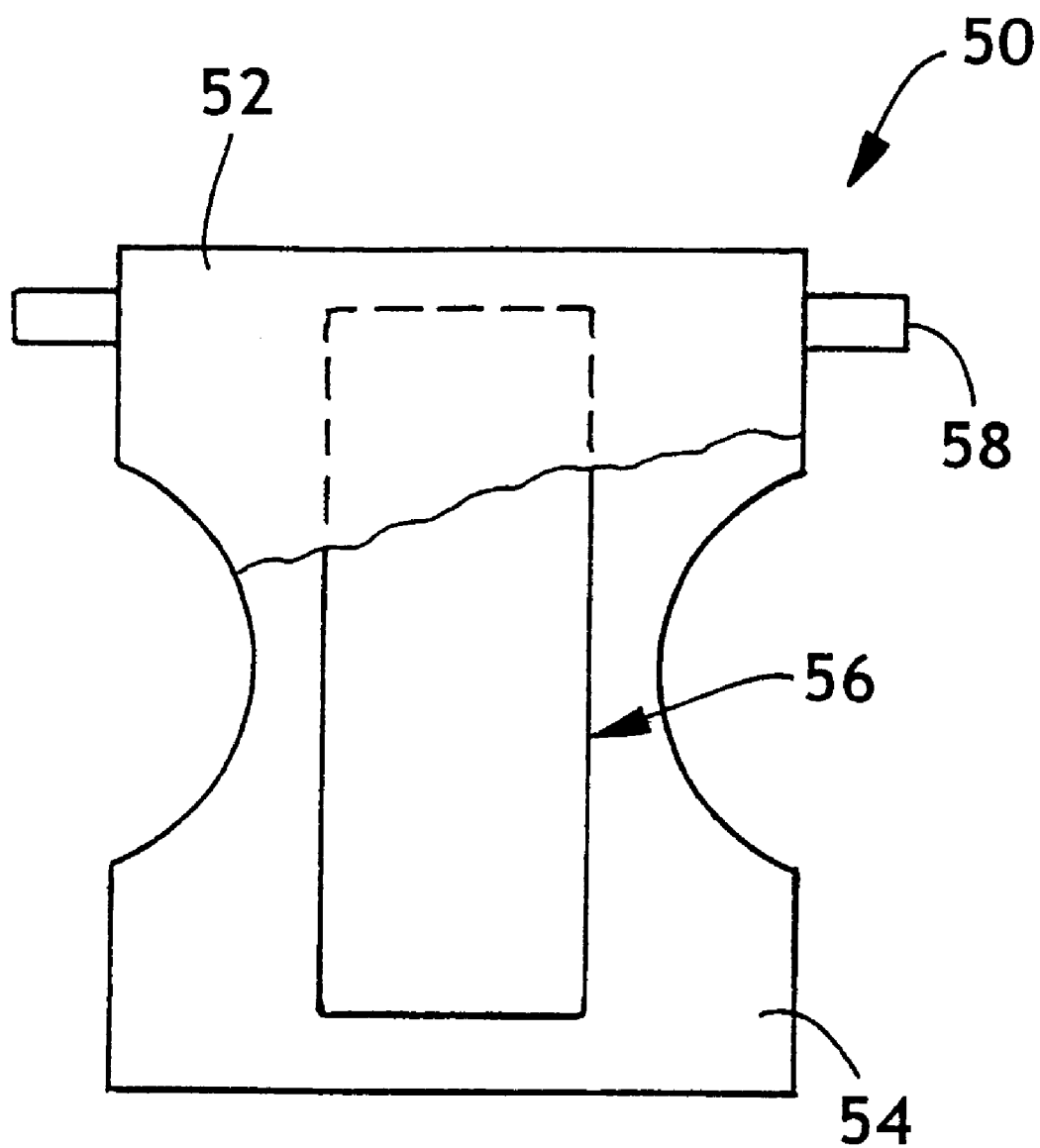
FIG. 3 is a top plan view of an exemplary personal care article, in this case a diaper, which may utilize a laminate according to the present invention.

As has been stated previously, film/nonwoven web laminates may be used in a wide variety of applications not the least of which includes personal care absorbent articles such as diapers, training pants, incontinence devices and feminine hygiene products such as sanitary napkins. An exemplary article, in this case a diaper 50, is shown in FIG. 3 of the drawings. Referring to FIG. 3, most such personal care absorbent articles include a liquid permeable top sheet or liner 52, a back sheet or outer cover 54 and an absorbent core 56 disposed between and contained by the top sheet and back sheet. Articles such as diapers may also include some type of fastening means such as adhesive fastening tapes 58 or mechanical hook and loop type fasteners to maintain the garment in place on the wearer. The fastening system may contain stretch material to form stretch ears for greater comfort.

Film/nonwoven web laminates may be used to form various portions of the article 50 including, but not limited to, the top 52 and back sheet 54. When using the film/nonwoven web laminate as an outercover, it is usually advantageous to place the nonwoven side facing out away from the user. In addition, in such embodiments it may be possible to utilize the nonwoven portion of the laminate as the loop portion of the hook and loop combination.

Other uses for the filled film and breathable film/nonwoven web laminates according to the present invention include, but are not limited to protective work wear such as surgical drapes and gowns, coveralls, lab coats and other articles of clothing.

As will be explained in more detail below, a surprising and unexpected improvement of the present invention lies in its increase in tear strength of the produced nonwoven web/film laminate as measured through numerous testing protocols. These improvements in tear strength are transferred to the articles of manufacture utilizing the laminates as a structural component, such as personal care articles and protective workwear. An advantage of the present invention lies in that tear strength is improved using a rapid in-line process, and without the use of relatively more expensive materials.

The present invention is further described by the examples which follow. Such examples, however, are not to be construed as limiting in any way either the spirit or the scope of the present invention.

EXAMPLES

A series of materials were prepared in accordance with the previously described process including conventional Ziegler Natta catalyzed polypropylene spunbond (designated as Z-N PP), and metallocene-catalyzed polypropylene spunbond (designated as Met PP) as support layers. The materials utilized in the nonwoven web/film laminate are described in the following Table 1.

TABLE 1

| Polymer Name | Polymer Type | Company Source | Use | Fiber Size | Melt flow Rate |
|---|---|---|---|---|---|
| 3854 | Metallocene-catalyzed Polypropylene | Exxon Chemical Company | Spun bond layer | 0.8 osy | 24 for pellets; 30–32 of fiber/fabric form |
| 3155 | Conventional Ziegler Natta catalyzed polypropylene | Exxon Chemical Company | Spun bond layer | 0.8 osy | 35 in pellet, 45 in fiber/fabric form |
| 50% CaCO3-50% LLDPE Core EVA/Catalloy PP Skin | 17.7 gsm | Huntsman | Film layer | 17.7 gsm | |

Example Conditions

Spunbond material was introduced into the spunbond extruders. For instance, Exxon 3854 metallocene polypropylene was introduced. The throughput of the spunbond was approximately 0.7 grams per hole per minute (GHM). The melt temperature for the spunbond is typically around 450° F. The spunbond calender and HAK settings were optimized for metallocene-catalyzed materials. The typical calender spunbond temperature is around 310–330° F. in the bonding rolls. The HAK temperature is usually held between 220–240° F. The MDO settings on the rolls were as follows: for the preheat 1-preheat 2 roll, the setting was at 76%, for the preheat 2-slow roll, the setting was at 98%, for the slow roll-fast roll, the setting was at 29%, for the fast roll-anneal 1 roll, the setting was at 100.5%, for the anneal 1-anneal 2 roll, the setting was at 100.5%, for the anneal 2-calender roll, the setting was at 101%, for the calender-winder roll, the setting was at 94%, and for the winder drum roll the setting was at 100.5%. The settings are expressed in percentages of the previous roll speed.

The denier of the spunbond produced was 2.0 dpf. Film was introduced from supply rolls and laminate was made with calender temperatures at 260/220° F. The top roll temperature is the first stated. Following the lamination of the film and spunbond layers in SF laminates, the following comparative tests were run for the materials, the results of which are expressed in Table 2. A comparison of data for a single layer of spunbond as well as necked bonded laminate materials is shown in Tables 3 and 4.

TABLE 2

|  |  | B.W. g/m^2 | Hydrohead 3rd drop | Elm. MD gm | Elm. CD gm | Trap-MD High gm | Trap-MD 1st gm | Trap-MD 1st & High gm | Trap-CD High gm | Trap-CD 1st gm | Trap-CD 1st & High gm |
|---|---|---|---|---|---|---|---|---|---|---|---|
| BSTL |  |  |  |  |  |  |  |  |  |  |  |
| Film | AVG | 62.707 | 108.100 |  |  |  |  |  |  |  |  |
|  | SD | 1.916 | 2.961 |  |  |  |  |  |  |  |  |
| BSTL - Laminates |  |  |  |  |  |  |  |  |  |  |  |
| Met PP/BSTL | AVG |  | 109.200 | 648.010 | 508.401 | 3174.142 | 3174.142 | 3174.142 | 2148.481 | 2148.481 | 2148.481 |
|  | SD |  | 22.235 | 113.270 | 70.183 | 234.318 | 234.318 | 234.318 | 136.889 | 136.889 | 136.889 |
| Z-N PPI BSTL | AVG |  | 37.350 | 391.208 | 294.280 | 2874.865 | 2874.865 | 2874.865 | 1664.258 | 1664.258 | 1664.258 |
|  | SD |  | 14.778 | 23.470 | 56.300 | 373.537 | 373.537 | 373.537 | 200.145 | 200.145 | 200.145 |

|  |  | Grab-MD PL gms | Grab-MD PS % | Grab-MD PEN gm-cm | Grab-CD PL gms | Grab-CD PS % | Grab-CD PEN gm-cm | WVTR gm/m^2 | Peel-CD Avg. Load gm | Peel-CD Scatter Index |
|---|---|---|---|---|---|---|---|---|---|---|
| BSTL |  |  |  |  |  |  |  |  |  |  |
| Film | AVG | 4114.606 | 104.823 | 26303.616 | 3961.742 | 149.988 | 27404.288 |  |  |  |
|  | SD | 132.451 | 15.270 | 4901.760 | 142.430 | 56.864 | 15935.616 |  |  |  |
| BSTL - Laminates |  |  |  |  |  |  |  |  |  |  |
| Met PP/BSTL | AVG | 8864.103 | 44.067 | 18620.928 | 5924.667 | 54.940 | 15492.096 | 1883.503 | 50.147 | 18.659 |
|  | SD | 323.640 | 7.269 | 4671.360 | 394.839 | 7.625 | 3356.928 | 119.314 | 3.082 | 3.474 |
| Z-N PP/BSTL | AVG | 7846.632 | 40.907 | 15395.328 | 5558.955 | 53.080 | 13632.768 | 1952.771 | 150.938 | 52.228 |
|  | SD | 855.682 | 6.876 | 3977.856 | 400.273 | 6.450 | 2606.976 | 131.931 | 12.756 | 11.702 |

TABLE 3

|  |  | g/m^2 | MD gm | CD gm | High gm | 1st gm | 1st & High gm | High gm | 1st gm | 1st & High gm |
|---|---|---|---|---|---|---|---|---|---|---|
| NBL - Facings |  |  |  |  |  |  |  |  |  |  |
| Z-N PP Facing (E5D47) | AVG | 26.400 | 222.606 | 304.029 | 2637.353 | 2528.845 | 2583.099 | 2152.193 | 2099.453 | 2125.823 |
|  | SD | 2.579 | 23.238 | 66.121 | 503.608 | 641.806 | 558.949 | 266.238 | 307.378 | 275.735 |
| Met PP (Exxon 3854) | AVG | 25.606 | 487.548 | 744.728 | 2859.539 | 2859.539 | 2859.539 | 2320.435 | 2320.435 | 2320.435 |
|  | SD | 0.673 | 83.675 | 81.567 | 348.034 | 348.034 | 348.034 | 159.721 | 159.721 | 159.721 |

|  |  | Grab-MD PL gms | Grab-MD PS % | Grab-MD PEN gm-cm | Grab-CD PL gms | Grab-CD PS % | Grab-CD PEN gm-cm |
|---|---|---|---|---|---|---|---|
| Z-N PP Facing (E5D47) | AVG | 8510.797 | 62.592 | 24023.808 | 6507.394 | 69.683 | 19998.720 |
|  | SD | 702.937 | 7.562 | 4689.792 | 1149.145 | 13.385 | 7411.968 |
| Met PP (Exxon 3854) | AVG | 8708.070 | 49.111 | 18952.704 | 5624.346 | 51.158 | 11674.368 |
|  | SD | 670.846 | 4.022 | 2795.904 | 556.121 | 4.498 | 2062.080 |

TABLE 4

|  |  | B.W. g/m^2 | Elm. MD gm | Elm. CD gm | Grab-MD PL gms | Grab-MD PS % | Grab-MD PEN gm-cm | Grab-CD PL gms |
|---|---|---|---|---|---|---|---|---|
| NBL - Laminates |  |  |  |  |  |  |  |  |
| Z-N PP/Met PE | AVG | 134.760 | 327.567 | 617.176 | 22993.164 | 31.384 | 36309.888 | 8441.366 |
|  | SD | 1.417 | 42.725 | 92.939 | 983.199 | 2.315 | 4308.480 | 354.427 |
| Met PP/ Met PE | AVG | 131.459 | 823.172 | 939.079 | 26900.490 | 23.399 | 30895.488 | 8708.070 |
|  | SD | 1.307 | 49.794 | 164.581 | 827.892 | 2.280 | 3837.312 | 477.602 |
| Z-N PP/Kraton G | AVG | 135.141 | 344.019 | 501.811 | 23341.863 | 29.886 | 34300.800 | 9382.153 |
|  | SD | 2.177 | 32.398 | 136.855 | 888.922 | 2.255 | 2597.760 | 516.002 |
| Met PP/Kraton G | AVG | 135.501 | 574.839 | 795.459 | 27255.443 | 21.793 | 29104.128 | 816.318 |
|  | SD | 2.249 | 175.921 | 179.766 | 1029.506 | 1.635 | 3363.840 | 422.511 |

|  | Grab-CD PS % | Grab-CD PEN gm-cm | Peel-CD Avg. Load gm | Peel-CD Scatter Index | 2 Cycle Percent Set % | 2 Cycle Elg. @ 1st 2K % | 2 Cycle Ld 1st 30% Up gm |
|---|---|---|---|---|---|---|---|

TABLE 4-continued

NBL - Laminates

| | | | | | | | | |
|---|---|---|---|---|---|---|---|---|
| Z-N PP/Met PE | AVG | 210.324 | 53070.336 | 1373.947 | 136.849 | 22.057 | 4.800 | 1115.358 |
| | SD | 4.476 | 3302.784 | 276.466 | 55.148 | 0.335 | 8.728 | 17.858 |
| Met PP/Met PE | AVG | 181.181 | 49189.248 | 895.560 | 93.561 | 25.432 | 4.675 | 875.487 |
| | SD | 6.930 | 5250.816 | 265.475 | 39.626 | 2.297 | 7.761 | 220.584 |
| Z-N PP/Kraton G | AVG | 229.907 | 62358.912 | 1145.373 | 92.912 | 19.648 | 1.238 | 756.200 |
| | SD | 7.032 | 5666.688 | 37.486 | 20.048 | 0.454 | 0.656 | 32.836 |
| Met PP/Kraton G | AVG | 202.926 | 45500.544 | 1029.247 | 92.531 | 20.900 | 1.562 | 637.112 |
| | SD | 16.693 | 5573.376 | 52.181 | 21.666 | 0.847 | 0.522 | 46.156 |

| | | 2 Cycle LD @ 1st Ext. gm | 2 Cycle Ld 1st 30% down gm | 2 Cycle Ld 2nd 30% Down gm | 2 Cycle Elg. @ Stop Ld. % | 2 Cycle Peak Load gm | 2 Cycle Elg. @ Peak % |
|---|---|---|---|---|---|---|---|
| NBL - Laminates | | | | | | | |
| Z-N PP/Met PE | AVG | 2123.518 | 153.732 | 124.477 | 99.661 | 9715.730 | 322.470 |
| | SD | 54.020 | 6.751 | 6.689 | 0.890 | 358.075 | 7.860 |
| Met PP/Met PE | AVG | 1925.214 | 94.079 | 69.819 | 107.033 | 8323.770 | 273.590 |
| | SD | 256.910 | 43.015 | 35.625 | 13.313 | 240.789 | 24.328 |
| Z-N PP/Kraton G | AVG | 1677.402 | 157.800 | 136.183 | 113.854 | 9850.300 | 371.120 |
| | SD | 88.797 | 6.456 | 5.558 | 4.148 | 289.354 | 14.175 |
| Met PP/Kraton G | AVG | 1567.763 | 121.407 | 105.194 | 116.720 | 8948.950 | 329.040 |
| | SD | 122.980 | 6.707 | 6.724 | 5.451 | 482.243 | 14.487 |

Test Methods

Basis weight (B.W.) This test determined the mass per unit area of the textile material by using a small 5×5 inch specimen. The measurement is typically expressed in grams per square meter (gsm) or ounces per square yard (osy).

Hydrohead (Hydrostatic Head): A measure of the liquid barrier properties of a fabric is the hydrohead test. The hydrohead test determines the height of water (in centimeters) which the fabric will support before a predetermined amount of liquid passes through. The test measures a fabric's resistance to water under static pressure. Under controlled conditions, a specimen is subjected to water pressure that increases at a constant rate until leakage appears on the material's lower surface. Water pressure is measured at the hydrostatic head height reached after the third sign of leakage. Values are recorded in millibars of pressure. When testing meltblown material a support net is used. A fabric with a higher hydrohead reading indicates it has a greater barrier to liquid penetration than a fabric with a lower hydrohead. The hydrohead test is performed according to Federal Test Standard 191A, Method 5514 using a Testest FX-3000 Hydrostatic Head Tester available from Marlo Industries, Inc., PO Box 1071, Concord, N.C.

Elmendorf Tear Test (Elem.): This test measures the average force required to propagate a tear starting from a cut slit in the specimen being tested, when part of the specimen is held in a clamp and an adjacent part is moved by the force of a pendulum freely falling in an arc. The specimen size is 2.5×4 and the test can be conducted in the CD or MD direction. In conducting the test, one of the following brand testers should be used. The Elmendorf Digi-tear brand Model 65–200, and Air clamps 65–200 obtained from the Thwing-Albert Instrument Company, Philadelphia, Pa., or the Lorentzen and Wettre brand, Model 09ED obtained from the Lorentzen Wettre Canada Inc., of Fairfield, N.J., or Textest FX 3700 brand (Digital Elmendorf) obtained from Schmid Corporation of Spartanburg, S.C.

Trap Tear Test (Trapezoid Tear (Trap)): The trapezoid or "trap" tear test is a tension test applicable to both woven and nonwoven fabrics. The entire width of the specimen is gripped between clamps, thus the test primarily measures the bonding or interlocking and strength of individual fibers directly in the tensile load, rather than the strength of the composite structure of the fabric as a whole. The procedure is useful in estimating the relative ease of tearing of a fabric. It is particularly useful in the determination of any appreciable difference in strength between the machine and cross direction of the fabric. The test measures the fabric resistance to tear propagation under a constant rate of extension. A fabric cut on one edge is clamped along nonparallel sides of a trapezoidal shaped specimen and is pulled, causing a tear propagation in the specimen perpendicular to the load. The test can be conducted in either the MD or CD direction. In conducting the trap tear test, an outline of a trapezoid is drawn on a 3 by 6 inch (75 by 152 mm) specimen with the longer dimension in the direction being tested, and the specimen is cut in the shape of the trapezoid. The trapezoid has a 4 inch (102 mm) side and a 1 inch (25 mm) side which are parallel and which are separated by 3 inches (76 mm). A small preliminary cut of ⅝ inches (15 mm) is made in the middle of the shorter of the parallel sides. The specimen is clamped in, for example, an Instron Model™ (a constant-rate-of-extension tester), available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154, which have 3 inch (76 mm) long parallel clamps. The specimen is clamped along the non-parallel sides of the trapezoid so that the fabric on the longer side is loose and the fabric along the shorter side taut, and with the cut halfway between the clamps. A continuous load is applied on the specimen such that the tear propagates across the specimen width. It should be noted that the longer direction is the direction being tested even though the tear is perpendicular to the length of the specimen. The force required to completely tear the specimen is recorded in pounds with higher numbers indicating a greater resistance to tearing. The test method used conforms to ASTM Standard test D1117–14 except that the tearing load is calculated as the average of the first and highest peaks recorded rather than the lowest and highest peaks. Five specimens for each sample should be tested. The data presented include first and high peak values. This procedure also conforms to Method 5136, Federal Test Methods Standards No. 191 issued in December 1968. The difference between the ASTM and the Federal procedure is in the final calculation of tearing load. In the ASTM procedure, tearing load is calculated as the average of the highest and lowest peaks; in the Federal method, the tearing load is the average of the five highest peaks recorded. Alternatively, a Sintech Tensile Tester may be used in the procedure.

Grab Tensile (Grab): This test measures the effective tensile strength and stretch of a material. A one square inch area is clamped at both ends of a 4×6 inch specimen. The specimen is pulled at a constant rate of extension to obtain results before the point of rupture. The test is a measure of breaking strength and elongation or strain of a fabric when subjected to unidirectional stress. This test is known in the art and conforms to the specifications of ASTM standards D-5034-92 and D-5035-92, and INDA IST 110.1-92, using a Constant Rate of Extension Tensile Testing Machine. This test also conforms to Method 5100 of the Federal Test Methods Standard 191A. The results are expressed in pounds to break and percent stretch before breakage. Higher numbers are indicative of a stronger, more stretchable fabric. The term "load" means the maximum/peak load or force, expressed in units of weight, required to break or rupture the specimen in a tensile test. The term "peak strain", "total energy" or "peak energy" (PEN) means the total energy under a load versus elongation curve as expressed in weight-length units. The term "elongation" or "percent stretch" means the increase in length of a specimen during a tensile test. Values for grab tensile strength and grab elongation are obtained using a specified width of fabric, usually 4 inches (102 mm), clamp width and a constant rate of extension. The sample is wider than the clamp to give results representative of effective strength of fibers in the clamped width combined with additional strength contributed by adjacent fibers in the fabric. The specimen is clamped in, for example, an Instron Model™, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154, which have 3 inch (76 mm) long parallel clamps. This closely simulates fabric stress conditions in actual use. The test can be conducted on wet or dry samples in the CD or MD directions. Alternatively, a Sintech Tensile Tester may be used, available from Sintech Corp., 1001 Sheldon Dr. Cary, N.C. Higher numbers in this test indicate a stronger, more stretchable fabric.

Standard Deviation (SD): Standard deviation as used in these examples represents a measure of dispersion and measures the average distance between a single observation and its mean. This is useful for understanding how variable a set of data may be. For example, the standard deviation may be used to allow one to predict failure rates and/or to determine how much variability is acceptable in a final product. The Standard Deviation for each sample was calculated in accordance with the following equation.

The use of n–1 in the denominator instead of the more natural n was used because if n (instead of n–1) were used, a biased estimate of the population standard deviation would result. The use of n–1 corrects for this bias with small sample sizes.

The formula for standard deviation is:

$$\sqrt{\frac{\sum (x_i - \bar{x})^2}{n-1}}$$

In the formula, "On" is the count of the number of observations. The distance from each observation ($x_i$) to the calculated average (x-bar) provides the basis for measuring variability. The closer these observations are to the average, the smaller the standard deviation. If all observations are the same, the standard deviation would be zero. The deviations are squared due to the average being the "fulcrum" of the data (a balance point between those observations greater than the average and those less than the average). If these deviations were not squared, the sum would be zero. The square root of the sum is then taken to get the value back into the units of the original data.

Breathability Test (WVTR): A measure of the breathability of a fabric is the water vapor transmission rate (WVTR). Circular samples measuring three inches (7.6 cm) in diameter are cut from each of the test materials, and a control of a piece of CELGARD® 2500 sheet from the Hoechst Celanese Corporation of Charlotte, N.C. CELGARD® 2500 sheet is a microporous polypropylene sheet. Three samples are prepared for each material. The test dish is a number 68–1 Vapometer pan distributed by Thwing-Albert Instrument Company of Philadelphia, Pa. One hundred milliliters of water are poured into each Vapometer pan and individual samples of the test materials and control material are placed across the open tops of the individual pans. Screw-on flanges are tightened to form a seal along the edges of the pan, leaving the associated test material or control material exposed to the ambient atmosphere over a 6.5 centimeter diameter circle having an exposed area of approximately 33.17 square centimeters. The pans are placed in a forced air oven at 100° F. (32° C.) for 24 hrs. The oven is a constant temperature oven with external air circulating through it to prevent water vapor accumulation inside. A suitable forced air oven is, for example, a Blue M Power-O-Matic 60 oven distributed by Blue M Electric Company of Blue Island, Ill. Prior to placement in the oven the pans are weighed. After 24 hours, the pans are removed from the oven and weighed again. The preliminary test water vapor transmission rate values are calculated as follows:

Test WVTR=(grams weight loss over 24 hours)×315.5 g/m²/24 hours.

The relative humidity within the oven is not specifically controlled.

Under predetermined set conditions of 100° F. (32° C.) and ambient relative humidity, the WVTR for the CELGARD® 2500 control has been defined to be 5000 grams per square meter for 24 hours. Accordingly, the control sample is run with each test and the preliminary test values are corrected to set conditions using the following equation:

WVTR=(Test WVTR/control WVTR)×(5000 g/m²/24 hours)

Peel Strength Test (Peel): This test determines the bond strength between component layers of bonded or laminated fabrics. Bond strength is the tensile force required to separate the component layers of a textile under specified conditions. In peel or delamination testing a laminate is tested for the amount of tensile force required to pull a film layer apart from a nonwoven web layer. Values for the peel strength are obtained using a width of fabric sample in approximately 6×4 inch specimens (6 inch in the MD direction). The plies of the specimens are manually separated for a distance of about 2 inches along the length of the specimen. One layer is then clamped into each jaw of a tensile testing machine, and then subjected to a constant rate of extension. The maximum force (i.e. peak load) needed to completely separate the component layers of the fabric is determined. Two clamps, each with two equal sized jaws, each measuring 1 inch parallel to the direction of load application and 4 inches perpendicular to the application of load are used. The average peak load of a series of samples is calculated. Results are expressed in units of weight with higher numbers indicating a stronger bonded fabric. The sample is clamped, for example in an Instron Model™, 1000, 1122, or 1130 available from the Instron Corporation, 2500 Washington St., Canton, Ma. 02021, or a Sintech Tensile Tester, Sintech QAD or Sintech Testworks available from Sintech, Inc., P.O. Box 14226, Research Triangle Park, N.C. 27709 or a Thwing-Albert, Model INTELLECT II, available from Thwing-Albert Instrument Company, 10960 Dutton Road, Philadelphia, Pa. 19154. The sample is then pulled apart for a distance of 2 inches at 180 degrees of separation and the average peel strength recorded in grams. A constant rate of extension is applied of 12±0.4 in./min (300±10 mm/min). The center of the CD web width of the film side of the sample is covered with a 4 inch wide masking tape or some other suitable material in order to prevent the film from ripping apart during the test. The masking tape is only on one side of the laminate and so does not contribute to the peel strength of the sample. For the purposes of this test the scatter index is the standard deviation of all of the data points collected in the specified peel region. The peel strength is the average force, expressed in grams, that is required to separate the bonded fabric at 180 degrees angle over a distance of two inches.

Results

Utilizing the inventive method, a laminate is produced with increased tear strength. The tear strength (as expressed through various Grab Tensile tests) is much higher than expected for film/nonwoven web laminates incorporating metallocene-catalyzed polypropylene rather than conventional Ziegler-Natta catalyzed polypropylene. Specifically, the strength is much higher than expected for metallocene-catalyzed inelastic polypropylene obtained under the designation 3854 from the Exxon Chemical Company. This increased tear strength is especially apparent in reviewing the Peak Energy test values for the metallocene-catalyzed laminates and comparing them to the values for the Ziegler-Natta catalyzed polypropylene laminate materials in Table 2. These increased tear strength values are even more surprising in view of the Peak Energy test results for the single spunbond facing samples and the facing samples in necked bonded laminates as seen in Tables 3 and 4. In each of these materials, the Peak Energy values were higher for the Ziegler-Natta catalyzed materials as opposed to the metallocene-catalyzed materials.

Furthermore, use of metallocene-catalyzed polyolefins allows for finer fiber which appears to aid in simultaneous bonding and lamination. It is theorized that such in-line processing avoids the high crystallinity which is present in aged or pre-formed spunbond. The resulting laminate provides improved tear resistance properties as can be seen through various test measures. This improvement is in deference to the higher temperatures and pressures necessary to thermally bond metallocene catalyzed based polypropylene spunbond fabric. Five to ten degrees higher bond temperatures are normally required for this polymer, which reduces tensile strength. While not intended to be limited by theory, it is theorized that the spunbond fibers are able to withstand the heat at the bond points without becoming brittle and yet transfer enough heat to the film component. Even at the same fabric strength, the tear resistance is higher.

Therefore, polyolefins (i.e. polypropylene) with narrow molecular weight distribution (i.e. single site catalyst) enable production of meltspun fibers with significantly enhanced mechanical properties despite the fibers being more difficult to bond thermally. An in-line process utilizing these materials produces a composite with better than expected tear strength attributes.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed:

1. A breathable barrier film and nonwoven laminate with improved tear strength over comparable laminates utilizing conventional catalyzed propylene nonwoven webs, comprising: A layer of inelastic spunbond polyolefin fibers and a layer of breathable film wherein the spunbond layer is of a single site catalyzed polyolefin; and the film includes a polyolefin.

2. A breathable barrier film and nonwoven laminate with improved tear strength over comparable laminates utilizing conventional catalyzed propylene nonwoven webs commprising: A layer of inelastic spunbond polyolefin fibers and a layer of breathable film wherein the spunbond layer is of inelastic metallocene-catalyzed polypropylene fibers of less than 2.5 dpf; and the film includes a polyolefin, and further wherein the level of breathabiliy is greater than 250 g/m$^2$/24 hours.

3. The breathable barrier film andnonwoven laminate of claim 2 wherein the level of breathability is greater than 1000 g/m$^2$/24 hours.

4. The breathable barried laminate of claim 2 wherein tear strength is measured in accordance with a grab tensile test method.

5. The breathable barrier laminate of claim 4 wherein tear strength is measured in accordance with a peak energy test and such value is greater than 16,000 In-Lb in the machine direction.

6. The breathable barrier laminate of claim 2 further including a second layer of inelastic spunbond polyolefin fibers on a side of the breathable film layer opposite that of the first spunbond layer.

7. A personal care absorbent article selected from the group consisting of diapers, training pants, feminine hygiene products, and incontinence devices comprising the laminate of claim 2.

8. A personal care absorbent article comprising:
   a. a liquid permeable top sheet;
   b. a back sheet;
   c. an absorbent core disposed between said top sheet and said back sheet; wherein either said top sheet or said back sheet comprises the laminate of claim 2.

9. Protective workwear selected from the group consisting of surgical drapes and gowns, coveralls, and lab coats comprising the laminate of claim 2.

* * * * *